United States Patent [19]

Yardley et al.

[11] 4,017,637

[45] Apr. 12, 1977

[54] BENZYLAMINE ANALGESICS

[75] Inventors: John P. Yardley, King of Prussia; Peter B. Russell, Villanova, both of Pa.

[73] Assignee: American Home Products Corporation, New York, N.Y.

[22] Filed: Aug. 25, 1975

[21] Appl. No.: 607,088

Related U.S. Application Data

[60] Division of Ser. No. 345,037, March 26, 1973, Pat. No. 3,928,626, which is a continuation-in-part of Ser. No. 241,613, April 6, 1972, abandoned.

[52] U.S. Cl. .............................. 424/311; 424/305; 424/330
[51] Int. Cl.$^2$ .............. A61K 31/135; A61K 31/22; A61K 31/215
[58] Field of Search ................... 424/305, 311, 330

[56] References Cited

UNITED STATES PATENTS

| | | | |
|---|---|---|---|
| 3,567,765 | 3/1971 | Thiele | 424/311 |
| 3,644,641 | 2/1972 | Marshall | 424/311 |
| 3,652,589 | 3/1972 | Flick | 424/311 |

*Primary Examiner*—Sam Rosen
*Attorney, Agent, or Firm*—Robert Wiser

[57] ABSTRACT

Reaction of benzalcyclanones with secondary amines affords aminobenzylcyclohexanones, which, upon reduction, yield aminobenzylcyclohexanols having potent analgesic activity. Epimeric aminobenzylcycloalkanols having analgesic activity are prepared by the reaction of C-phenyl nitrones with cycloalkenes to form benzisoxazoles, treatment with alkyl halide to form the corresponding benzisoxazolium halides, followed by hydrogenolysis.

9 Claims, 2 Drawing Figures

BENZYLAMINE ANALGESICS

This is a division of application Ser. No. 345,037, filed Mar. 26, 1973, now U.S. Pat. No. 3,928,626, which in turn is a continuation-in-part of application Ser. No. 241,613, filed Apr. 6, 1962, now abandoned.

BACKGROUND OF THE INVENTION

In U.S. Pat. No. 2,767,185 a process is described for the preparation of certain amino cyclanol compounds of the formula

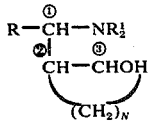

wherein $n$ is an integer from 3 to 5, R is a phenyl radical and $NR_2^1$ is a secondary amino group selected from the class consisting of the N-methyl-N-alkylamino and N-methyl-N-aralkylamino radicals, piperidino, morpholino, pyrrolidino and N'- alkylpiperazino radicals. These compounds, which are produced by the reaction of benzalcyclanones with appropriate secondary amines followed by reduction, were obtained as mixtures of two epimeric racemic modifications, that is a mixture of the racemates of the forms which are denoted cis and trans with respect to the configurations at the asymmetric carbon atoms labeled ② and ③ in the above formula. Several compounds where $NR_2^1$ was piperidino or N'-alkylpiperazino were separated into their two racemic modifications without identification. The two additional epimeric racemic modifications which are theoretically possible through opposite configuration at the asymmetric carbon atom labeled ① were not obtained. The specific utility ascribed to the products in this patent was the use of the N'-alkylpiperazine compounds as intermediates in the preparation of corresponding hexahydro-benzhydryl piperazines whose quaternary salts are stated to be powerful spasmolytics. This utility is further described in U.S. Pat No. 2,748,126, with specific reference to the use of the trans epimer.

In Baltzly, et al., J.A.C.S. 77, 624 (1955) the reaction of secondary amines with benzalcyclanones followed by reduction to afford aminocyclanols is further described, including the characterization by melting point of the cis and trans epimers of piperidino- and N'-alkyl-piperazino-benzylcyclohexanols. In russell et al, J.A.C.S. 77, 629 (1955), the method of establishment of the configuration of the epimeric piperidino- and N-alkylpiperazino-benzylcyclohexanols is described.

Huisgen, et al, Chem. Ber. 101, 2043 (1968) described the addition of C-phenyl nitrone to cyclopentene or cyclohexene to give a corresponding isoxazolidine and in the case of the cyclopentene, reduction to afford an α-methylamino-benzylcyclo- pentanol. The stereochemistry at the α-carbon atom was not described.

SUMMARY OF THE INVENTION

The invention sought to be patented in a principal process aspect resides in the concept of a method for producing analgesia in warm-blooded animals which comprises administering to a warm-blooded animal in need thereof an amount sufficient to produce analgesia in said warm-blooded animal of a compound of the formula:

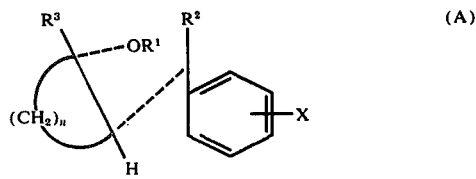

wherein $R^1$ is hydrogen, lower alkyl, or lower alkyl carbonyl; $R^2$ is lower alkylamino, N-lower alkyl-N-methylamino, N-phen- loweralkyl-N-methylamino, 1-pyrrolidinyl, 4-morpholino, N-lower alkenyl-N-methylamino, N-cycloalkylmethyl-N-methylamino, or N-oxo-N-lower alkyl-N-methylamino; $R^3$ is hydrogen or methyl; X is hydrogen, hydroxy, lower alkoxy, lower alkoxymethoxy, lower alkylcarbonyloxy, or halo; and $n$ is an integer of from 3 to 6; and the pharmacologically acceptable acid addition salts thereof.

The invention sought to be patented in a second process aspect resides in the concept of a method for producing analgesia in warm blooded animals which comprises administering to a warm blooded animal in need thereof an amount sufficient to produce analgesia in said warm blooded animal of a compound of the formula:

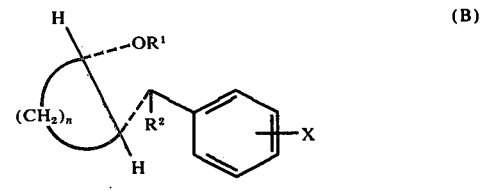

wherein $R^1$ is hydrogen, lower alkyl, or lower alkyl carbonyl; $R^2$ is lower alkylamino, N-lower alkyl-N-methylamino, N-phenloweralkyl- N-methylamino, N-lower alkenyl-N-methylamino, N-cycloalkyl- N-methylamino, or N-oxo-N-lower alkyl-N-methylamino; X is hydrogen, hydroxy, lower alkoxy, lower alkoxymethoxy, lower alkylcarbonyloxy, or halo; and $n$ is an integer of from 3 to 6; and the pharmacologically acceptable acid addition salts thereof.

The invention sought to be patented in a principal composition aspect resides in the concept of a compound of the formula:

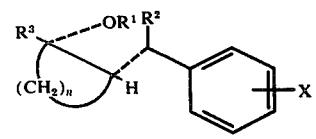

substantially free of the trans epimer; wherein $R^1$ is hydrogen, lower alkyl, or lower alkyl carbonyl; $R^2$ is lower alkylamino, N-lower alkyl-N-methylamino, N-phenloweralkyl-N-methylamino, N- lower alkenyl-N-methylamino, 1-pyrrolidinyl, 4-morpholino, N-cycloalkyl-methyl-N-methylamino, or N-oxo-N-lower alkyl-N-methylamino; $R^3$ is hydrogen or methyl; X is hydrogen, hydroxy, lower alkoxy, lower alkoxymethoxy, lower alkylcarbonyloxy, or halo; and $n$ is an integer of from 3 to 6; and the pharmacologically acceptable acid addition salts thereof.

The tangible embodiments of the principal composition aspect of the invention possess the inherent general physical properties in the free base form of being colorless to yellow oils, or solids, substantially insoluble in water, and generally soluble in organic solvents such as ether, benzene, hexane, acetone and pyridine. In the form of their acid addition salts they are generally white or off-white crystalline solids, appreciably soluble in water. Examination of the compounds produced according to the hereinafter described process reveals, upon infrared, ultraviolet, and nuclear magnetic resonance spectrographic analysis, spectral data supporting the molecular structure hereinbefore set forth. The aforementioned physical characteristics, taken together with the nature of the starting materials, the elemental analysis, and the products obtained therefrom, further confirm the molecular structure hereinbefore set forth.

The tangible embodiments of the principal composition aspect of the invention possess the inherent applied use characteristic of exerting analgesic effects in warm blooded animals as evidenced by pharmacological evaluation according to standard test procedures.

The invention sought to be patented in a second composition aspect resides in the concept of a compound of the formula:

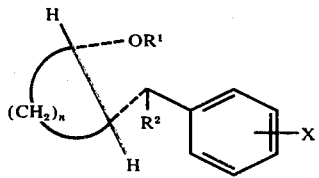

wherein $R^1$ is hydrogen, lower alkyl, or lower alkyl carbonyl; $R^2$ is N-lower alkyl-N-methylamino, N-phenyloweralkyl-N-methylamino, N-cycloalkylmethyl-N-methylamino, N-lower alkenyl-N-methylamino, or N-oxo-N-lower alkyl-N-methylamino; X is hydrogen, hydroxy, lower alkoxy, lower alkoxymethoxy, lower alkylcarbonyloxy, or halo; and n is an integer of from 3 to 6; and the pharmacologically acceptable acid addition salts thereof.

The tangible embodiments of the second composition aspect of the invention possess the inherent general physical properties in the free base form of being colorless to yellow oils or solids, substantially insoluble in water, and generally soluble in organic solvents such as ether, benzene, hexane, acetone and pyridine. In the form of their acid addition salts they are generally white or off-white crystalline solids, appreciably soluble in water. Examination of the compounds produced according to the hereinafter described process reveals, upon infrared, ultraviolet, and nuclear magnetic resonance spectrographic analysis, spectral data supporting the molecular structure hereinbefore set forth. The aforementioned physical characteristics, taken together with the nature of the starting materials, the elemental analysis, and the products obtained therefrom further confirm the molecular structure hereinbefore set forth.

The tangible embodiments of the second composition aspect of the invention possess the inherent applied use characteristic of exerting analgesic effects in warm blooded animals as evidenced by pharmacological evaluation according to standard test procedures.

The invention sought to be patented in a third composition aspect of the invention resides in the concept of a composition suitable for administration to a warm blooded animal comprising:

a. a compound of the formula:

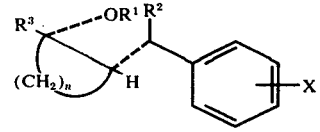

wherein $R^1$ is hydrogen, lower alkyl, or lower alkyl carbonyl; $R^2$ is lower alkylamino, N-lower alkyl-N-methylamino, N-phenyloweralkyl-N-methylamino 1pyrrolidinyl, 4-morpholino, N-lower alkenyl-N-methylamino, N-cycloalkylmethyl-N-methylamino, or N-oxo-N-lower alkyl-N-methylamino; $R^3$ is hydrogen or methyl; X is hydrogen, hydroxy, lower alkoxy, lower alkoxymethoxy, lower alkyl carbonyloxy, or halo; and n is an integer of from 3 to 6; and the pharmacologically acceptable acid addition salts thereof, and b. a pharmaceutically acceptable carrier.

The invention sought to be patented in a fourth composition aspect of the invention resides in the concept of a composition, suitable for administration to a warm-blooded animal, comprising:

a. a compound of the formula:

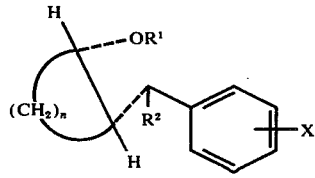

wherein $R^1$ is hydrogen, lower alkyl, or lower alkyl carbonyl; $R^2$ is lower alkylamino, N-lower alkyl-N-methylamino, N-phenyloweralkyl-N-methylamino, N-lower alkenyl-N-methylamino, N-cycloalkylmethyl-N-methylamino, or N-oxo-N-lower alkyl-N-methylamino; X is hydrogen, hydroxy, lower alkoxy, lower alkoxymethoxy, lower alkyl carbonyloxy, or halo; and n is an integer of from 3 to 6; and the pharmacologically acceptable acid addition salts thereof; and b. a pharmaceutically carrier.

BRIEF DESCRIPTION OF THE DRAWING

In describing the invention reference will be made in the following specification to the annexed drawings wherein.

DESCRIPTION OF THE PREFERRED EMBODIMENTS

Figure 1:
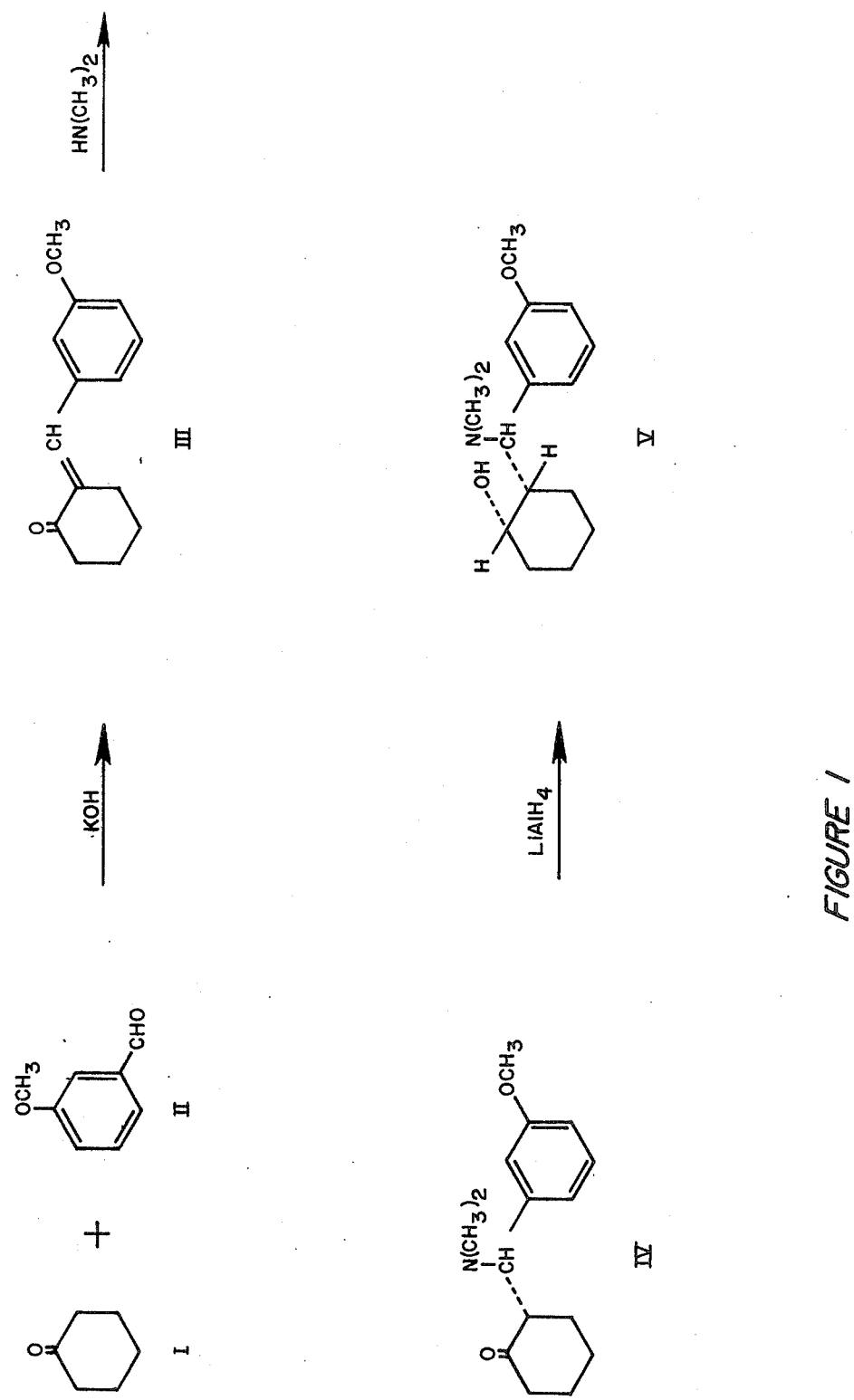
FIG. 1 illustrates schematically the reaction sequence for preparing a cis-aminobenzylcycloalkanol, specifically cis-2-($\alpha$-dimethylamino-m-methoxybenzyl)cyclohexanol.

Referring now to FIG. 1 wherein the compounds are assigned Roman numerals for identification, the starting materials for this process, i.e., the cycloalkanones (I) and benzaldehydes (II) are known in the art or may be prepared from known compounds by methods which would be obvious to those skilled in the art of chemistry, such as, for example the method described in Edwards et al., J. Chem. Soc. (c) 411 (1967). Reaction of I and II, in the presence of aqueous base, such as potassium hydroxide, yields the correspondingly substituted benzalcycloaklanone (III). While the temperature of reaction is not critical, the condensation is most conveniently effected at reflux temperature, and for optimum yield, under nitrogen. The product may be isolated from the reaction medium by such standard procedures as extraction with an organic solvent, such as diethyl ether, followed by washing, drying, and evaporation of the solvent, and distillation of the residue to obtain the product as an oil. The thus obtained benzalcycloalkanone is then reacted with the requisite amine in a non-reactive solvent such as diethyl ether to form the corresponding benzylcycloalkanone (IV). This reaction is conveniently carried out at room temperature in a pressure bottle, preferably using an excess of the amine reactant. After sufficient time has elapsed to insure optimum production of the benzylcycloalkanone product, the reaction mixture, or the isolated addition product, is added to a suspension of a reducing agent, such as a complex metal hydride, e.g., lithium aluminum hydride, sodium or potassium borohydride, lithium aluminum trimethoxy hydride, or diborane, in a non-reactive organic solvent, such as diethyl ether, and the mixture is then refluxed for several hours to form the corresponding benzylcycloalkanol product V. The product may then be isolated by means known to those skilled in the art. For example, the reaction mixture may be treated with dilute aqueous base, such as 3% sodium hydroxide, the organic phase separated from solids and the aqueous phase, followed by extraction with a dilute mineral acid such as dilute hydrochloric acid, extraction of the aqueous acid extract with basified solvent, such as ether, and washing and drying of the solvent phase followed by evaporation of the solvent. The thus obtained product, usually in oil, generally comprises two epimeric forms which are then further separated.

The compounds of the invention have three asymmetric carbon atoms, as indicated in the following formula:

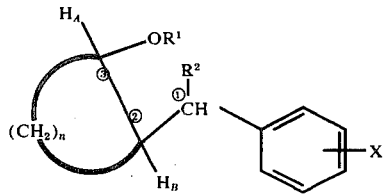

and theoretically should be capable of existing in eight optically active forms, or four racemic modifications. In the above described process, however, not all of these are obtained, and the product of the reduction step is essentially a mixture of but two racemic modifications (i.e., two epimeric forms and their enantiomers). The precursor amino ketones (IV)k contain two asymmetric centers and are theoretically capable of existing in two racemic modifications. However, so long as the amine ketones are not permitted to remain in the reaction system of their formation for considerable periods of time, for example three days or longer, only one epimer is isolated. On reduction of the carbonyl group, a new asymmetric center is formed, leading to two epimeric racemic modifications, $H_AH_B$ cis and $H_AH_B$ trans, which may be depicted according to the following convention:

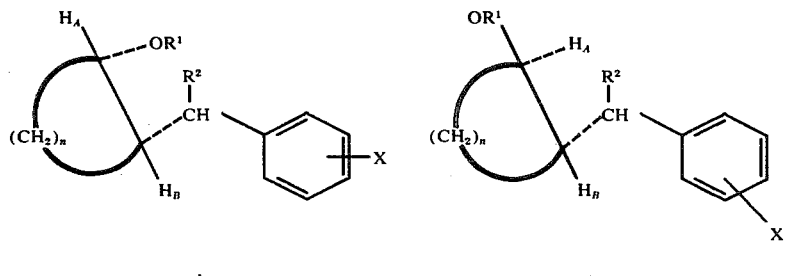

cis                                    trans

Where used in this specification and claims, the term "cis" as applied to the compounds of the invention denotes the epimer having the $H_AH_B$ cis relationship.

The cis and trans epimers as above produced may be separated by use of techniques known to those skilled in the art, such as fractional crystallization, or preferably chromatography. They are conveniently separated chromatographically on Woelm Alumina, for example neutral activity, grade III, in a column prepared in benzene/hexane, 1:1. Elution may be accomplished by use of such systems as benzene/hexane followed by benzene/ether, or benzene/hexane followed by benzene, followed by benzene/ether. The trans isomer will be eluted first, usually in the first solvent mixture, followed by the cis form in the second.

Another efficacious system is the use of a Woelm alumina column prepared out of chloroform, with the trans epimer being eluted first with chloroform or chloroform containing 5–10% acetone, and the cis component being eluted with methanol after cutting the column directly above the cis component. Visualization of the cis component is accomplished by means of ultraviolet light. The optimum chromatographic systems for most efficacious separation will, of course, vary with the specific compounds being separated, but the choice of such optimum systems is well within the skill of a trained chemist. The cis and trans configuration may be differentiated by virtue of a narrower NMR signal in the cis.

It has been found that the above step for separation of the cis form will not always be necessary. Where diborane is used for the reduction of the intermediate aminoketone, the cis epimer is isolated substantially free of the trans form.

While the above process has been specifically described by reference to FIG. 1 which illustrates the preparation of a compound of formula A wherein $R^1$ is hydrogen, $R^2$ is dimethylamino, $R^3$ is hydrogen, and X is m-methoxy, it will be apparent to those skilled in the art of chemistry that any of the compounds as variously substituted within the scope of the invention wherein $R^3$ is hydrogen may be prepared by this process, as well as by modifications of this process which would be obvious to those skilled in the art. Thus, compounds where X is hydrogen, hydroxy, lower alkoxy, lower alkoxymethoxy, or halo may be prepared by employing the appropriately substituted benzaldehyde compound in the first step of the above- described process. Similarly, compounds where $R^2$ is lower alkylamino, N-lower alky-N-methylamino, N-lower alkenyl-N- methylamino, N-cycloalkylmethyl-N-methylamino, N-phenlower alky-N-methylamino, 1 -pyrrolidinyl, or 4-morpholino may be prepared by employing the appropriately substituted primary or secondary amine in the second reaction step. Compounds where $R^2$ is N-oxo-N-lower alkyl-N-methylamino are prepared by treating the corresponding products where $R^2$ is N-lower alky-N-methylamino with a peracid, such as m-chloroperbenzoic acid. Compounds where $R^1$ is lower alkylcarbonyl may be prepared by treating the corresponding products where $R^1$ is hydrogen with a lower alkyl carboxylic acid anhydride or a lower alkyl carboxylic acid chloride, and compounds where X is lower alkylcarbonyloxy may be prepared by treating the corresponding products where X is hydroxyl with such acylating agents. Compounds where $R^1$ is methyl may be prepared by treating the corresponding compound where $R^1$ is hydrogen with a strong base, such as butyl lithium, and methyl iodide. In addition to their synthesis from the correspondingly substituted benzaldehydes, compounds where X is hydroxy, in a preferred route, may be prepared by acid hydrolysis of a corresponding product wherein X is alkoxymethoxy. Compounds where X is hydroxy may be converted to compounds where X is methoxy by treatment with diaxomethane, or to compounds where X is lower alkoxy by reaction with the appropriate alkyl halide in the presence of base. The accomplishment of these and other modifications of the process described in FIG. 1 will be readily apparent to those skilled in the art of chemistry.

Compounds where $R^3$ is methyl are conveniently prepared by an alternate process in which the benzylcycloalkanone (IV) is treated with methyl Grignard reagent, e.g. methyl magnesium bromide under the customary conditions for Grignard addition to ketones, e.g. in ether at reflux for up to several hours. As in the general case of the synthesis of compounds wherein $R^3$ is hydrogen, the cis-epimer is formed in admixture with the trans-epimer, and may be separated therefrom by the same techniques.

Although compounds where $R^2$ is loweralkylamino may be prepared by use of the appropriate primary amine in the condensation step, it has been found that the use of a primary amine provides a reaction which is less stereospecific than that described for the use of secondary amines; as a result, there is formation of the second possible epimer at this stage in observable amounts, with concomitant decrease in yield of the desired epimer in the ultimate process step. For this reason, a modification of the general process is preferable in the synthesis of these secondary amine products. In this modification, the benzalcyclohexanone compound formed in the first reaction step is reacted with a benzyl loweralkyl amine to form the corresponding $\alpha$-(N-benzyl N-loweralkylamino)benzyl cycloalkanone, which is then reduced in the manner previously described to the corresponding cycloalkanol. Hydrogenolysis of this compound, for example with 10% palladium on charcoal in the presence of an acid, such as acetic acid, affords the desired $\alpha$-(loweralkylamino)-benzyl cycloalkanol. These latter compounds may also be used as intermediates in alternate means of synthesis of compounds wherein $R^2$ is N-lower alkyl-N-methylamino, N-lower alkenyl-N-methylamino, N-cycloalkyl-methyl-N-methylamino, or N-phenlower alkyl-N-methylamino. In this variation, the $\alpha$-(lower alkylamino)benzyl cycloalkanol is reacted with a carboxylic acid halide (for example acetyl chloride if the desired substituent $R^2$ is N-ethyl-N-methylamino) and the thus formed intermediate is reduced, for example with lithium aluminum hydride, to produce the desired product. A product wherein $R^2$ is N-lower alkenyl-N-methylamino may be obtained by alkylation of the corresponding compound wherein $R^2$ is methylamino with a lower alk-2-enyl halide. A particular method available for the production of compounds wherein $R^2$ is dimethylamino is reaction with either ethyl chloroformate or N,N'-carbonyl diimidazole to give respectively an N-methyl, carbethoxy urethane or cyclic urethane which on reduction, for example with lithium aluminum hydride, affords the desired product.

Figure 2:
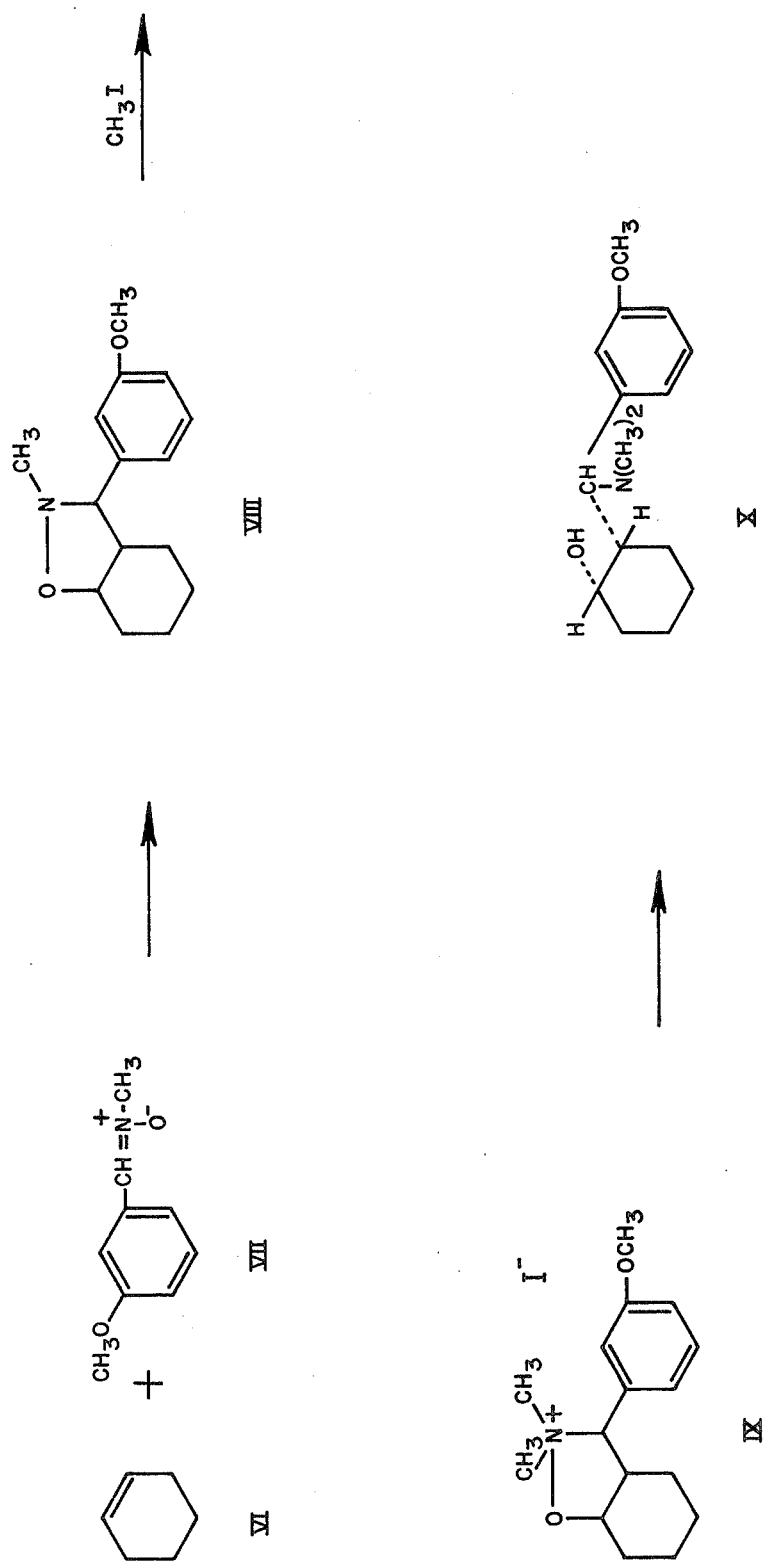
FIG. 2 illustrates schematically the reaction sequence for preparing an epi-cis-aminobenzylcycloalkanol, specifically epi-cis-2-($\alpha$-dimethylamino-m-methoxybenzyl) cyclohexanol.

Referring now to FIG. 2 (which illustrates the process for the synthesis of benzyl epimers of compounds produced by the process of FIG. 1), the starting materials are either known in the art or may be prepared from known compounds by methods which would be obvious to those skilled in the art of chemistry. The starting cycloalkenes (VI) are, of course, readily obtainable. The nitron (VIII) is readily prepared from N-alkylhydroxylamine and the appropriately substituted aldehyde. Reaction of the cycloalkene, preferably in excess, with the nitrone at an elevated temperature, for example at about 70° to 180° C. affords the benzisoxazole (VIII). Treatment of the benzisoxazole with an alkyl halide, such as methyl iodide, in a non-reactive solvent, such as tetrahydrofuran or diethyl ether, affords the corresponding benzisoxazolium halide (IX). The temperature of this reaction is unimportant and it is conveniently run at room temperature. Hydrogenolytic cleavage of IX affords the desired epi-cis-aminobenzylcycloalkanol (X). The hydrogenolysis is conveniently performed in a suitable non-reactive solvent, such as ethanol, using a hydrogenation catalyst, such as Raney nickel, and in the presence of a weak base, for example anhydrous sodium acetate.

As was stated above, the process illustrated in FIG. 1, which for the purposes of this specification will be called the amine condensation process, affords mixtures of two epimeric racemic modifications, namely the cis and trans isomers (having reference to the two asymmetric centers in the cycloalkyl ring) from which mixtures the desired cis-epimer is isolated. The compounds obtainable by said process, and whose formulae will be drawn according to the following convention

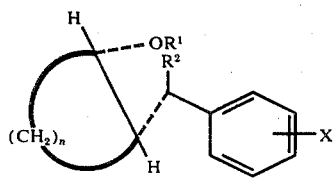

are the compounds of the principle process aspect and principle and third composition aspects of the invention. For purposes of this specification and claims these compounds will be considered to be of the "normal" configuration, and will be named without additional prefix. The compounds obtainable by the process illustrated in FIG. 2, which for the purposes of this specification will be called the nitrone process, possess exclusively the cis configuration with reference to the two asymmetric centers in the cycloalkane ring. However, it has been determined that there are produced compounds which are diastereo-isomers of the compounds of "normal" configuration, and therefore must be epimers having the opposite configuration at the benzyl carbon. These compounds obtained by the nitrone process, and whose formulae will be drawn according to the convention

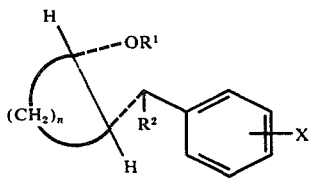

are the compounds of the second process aspect and the second and fourth composition aspects of the invention. For purposes of this specification and claims these compounds will be considered to be of the "epi" configuration, and will be named with the prefix "epi-".

While the nitrone process has been specifically described by reference to FIG. 2 which illustrates the preparation of a compound of formula B wherein $R^1$ is hydrogen, $R^2$ is dimethylamino and X is m-methoxy, it will be apparent to those skilled in the art of chemistry that any of the compounds as variously substituted within the scope of the invention may be prepared by this process or by modifications of this process which would be obvious to those skilled in the art. Thus compounds where X is hydrogen, hydroxy, lower alkoxy, lower alkoxymethoxy, or halo may be prepared by using as starting material the appropriate substituted nitrone. Compounds where $R^2$ is N-lower alkyl-N-methylamino may be prepared by substituting for methyl iodide the appropriate lower alkyl halide in the second step of the process.

Compounds where X is hydroxy may be obtained by hydrolysis with acid of products wherein X is alkoxymethoxy. These in turn may be acylated as with a lower alkyl carboxylic acid anhydride or a lower alkyl carboxylic acid chloride to afford the corresponding compound wherein X is lower alkylcarbonyloxy. Compounds where $R^1$ is lower alkyl carbonyl may similarly be prepared from compounds where $R^1$ is hydrogen by treatment with such acylating agents. Compounds where $R^1$ is methyl may be prepared by treating the corresponding compound where $R^1$ is hydrogen with a strong base, such as butyl lithium, and methyl iodide. Compounds where X is hydroxy may be comverted to compounds where X is methoxy by treatment with diazomethane, or to compounds where X is lower alkoxy by reaction with the appropriate alkyl halide in the presence of base. Compounds where $R^2$ is N-oxo-N-lower alkyl-N-methylamino are prepared by treating the corresponding compound where $R^2$ is N-lower alkyl-N-methylamino with a peracid, such as m-chloroperbenzoic acid.

In the practice of the nitrone process it is found, where n in formula B is 3 or 4, that the desired eip-cis-product is obtained exclusively. Where n is 5 or 6, the epi-cis product is obtained in admixture with varying amounts of the "normal" cis-product. Separation of these diasteroisomers may be effected by any of the techniques known in the art for effecting such separations, such as chromatography or fractional crystallization. Identification of the separated diastereoisomers may be obtained by comparison of their physical properties with those of the normal diastereoisomer prepared by the amine condensation process.

Compounds of the formula B wherein $R^2$ is lower alkylamino are prepared by reduction of the corresponding benzisoxazole (produced in the first step of the process illustrated in FIG. 2) by means of hydrogenation using Raney nickel. This hydrogenation is not particularly selective, and it is found that the products are frequently mixtures of isomers. The desired epi-cis-compound can readily be separated from the other isomers which may be present by routine means such as chromatography. The desired epi-cis-isomer can be identified in the manner described previously for other compounds of the invention. If desired, the thus-obtained epi-cis-compounds wherein $R^2$ is lower alkylamino can be converted to compounds where $R^2$ is N-lower alkyl-N-methylamino, N-lower alkenyl-N-methylamino, N-cycloalkylmethyl-N-methylamino, or N-phenlower alkyl-N-methylamino in the same manner as described above for the normal epimers.

Where used in this specification and claims, the terms "lower alkyl" and "lower alk-" mean straight and branched chain hydrocarbon radicals containing from 1 to about 8 carbon atoms, such as methyl, ethyl, n-propyl, isopropyl, and the like. The term "lower alkenyl" means mono-alkenes of from 1 to about 8 carbon atoms, which may also be straight or branched chain. The term "cycloalkyl" means a cyclic hydrocarbon radical of from 3 to about 6 carbon atoms, illustrative members of which are cyclopropyl, cyclobutyl, and the like. The term "phenloweralkyl" means a phenyl group attached thru an alkyl radical of 1 to 4 carbon atoms.

It will be apparent to those skilled in the art that the cycloalkanone and cycloalkene starting materials used in the synthesis of the compounds of the invention may bear substituent groups which are unaffected by the synthetic processes, such as methyl, methoxy, chloro, trifluoromethyl, etc., and these variations are the full equivalents of the compounds and processes particularly described.

In practicing the process aspects of inducing analgesia in warm-blooded animals, the compositions can be administered in a variety of dosage forms, either orally or parenterally. The dosage requirements will vary with the particular composition being employed, the severity and nature of the pain, and the animal being treated.

With large animals (about 70 kg body weight), by the oral route, the dose is from about 2 to about 40 mg, and preferably from about 10 to about 25 mg, every four hours, or as needed. By the intramuscular route, the dose is from about 1 to about 20 mg, as needed. Ideally, therapy should be initiated with lower dosages, the dosages thereafter being increased until the desired analgesia is obtained.

For unit dosages, the active ingredient can be compounded into any of the usual oral dosage forms including tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant.

The basic compounds of the invention may be used in the form of the free base or in the form of any pharmacologically acceptable acid addition salt thereof. These salts may be simply formed by reaction of the free base form with an equivalent amount of any acid in which the acid addition salt formed would be essentially non-toxic under the conditions of use. Illustrative of these salts are the hydrochloride, hydrobromide, fumarate, maleate, succinate, sulfate, phosphate, tartrate, acetate, citrate, etc. For parenteral administration it is convenient to employ the compounds of the invention in the form of their pharmaceutically acceptable acid-addition salts. These salts are water soluble, and may be readily incorporated into preparations suitable for injection.

The following examples further illustrate the best mode contemplated by the inventors of carrying out their invention:

EXAMPLE 1 m-Methoxymethoxybenzalcyclohexanone m-Methoxymethoxybenzaldehyde (167 g., 1.0 mole) and cyclohexanone (318 ml., 3.0 moles) were refluxed for 4 hours under nitrogen with a solution of potassium hydroxide (50 g., 0.89 moles) in water (1 liter). After cooling the oily layer was extracted with ether (twice). The ether solution was washed with water (thrice), brine, dried ($Na_2SO_4$), and evaporated. The residue was distilled and the product obtained as a yellow oil (132 g.), b.p. 173°–176° at 0.3 mm.$\lambda_{max}^{95\% EtOH}$ 287 m$\mu$($\epsilon$13,000). $\nu_{KBr}$ 1685, 1600, 1580 cm$^{-1}$. NMR ($CDCl_3$): $\delta$ 5.2 (2H singlet, —O$\underline{CH}_2$O), 3.48 (3H singlet, —O$\underline{CH}_3$).

EXAMPLE 2

Cis-2-($\alpha$-Dimethylamino-m-Methoxybenzyl)Cyclohexanol

A solution of m-methoxybenzalcyclohexanone (50 g. 2.31 × 10$^{-1}$ moles) in ether (50 ml.) was cooled to −5° in a pressure bottle and treated with 20 ml. dimethylamine (3 × 10$^{-1}$ moles). The bottle was stoppered and left at room temperature during 60 hours. The above reaction was performed in duplicate (IR monitoring indicates the mixture attains an equilibrium concentration in which the $\beta$-dimethylamino ketone addition product is favored over the m-methoxybenzalcyclohexanone by a ratio of ca. 2:1). the combined total reaction mixtures were added dropwise under nitrogen to a stirred suspension of $LiAlH_4$ (20 g.) in ether (1.2 liters) and the mixture was refluxed during 4 hours. The ice cooled reaction mixture was treated with 3% aqueous NaOH solution (100 ml.) and filtered. The precipitated solids were washed with boiling ether and the combined filtrates evaporated to approximately 1 liter. The ether layer was extracted (twice) with an excess of dilute HCl followed by a water extraction. The combined aqueous extracts were back extracted with ether, basified with 50% NaOH and extracted with ether (twice). The ether layers were washed with brine and evaporated to an oil (50 g.) shown by gle to consist predominantly (96%) of two components. 32 g. of the residue were chromatographed on a Woelm alumina column (900 g. neutral activity Grade III), built in benzene-hexane (1:1). Benzene-hexane fractions (1:1 and 2:1) eluted the major component trans-2-($\alpha$-dimethylamino-m-methoxybenzyl)cyclohexanol (20 g.) NMR ($CDCl_3$): $\delta$ 2.28 (GH singlet N($\underline{CH}_3$)$_2$), 3.0 (1H doublet J=3 cps $\underline{CH}$ N(Me)$_2$), 3.3–3.7 (1H broad multiplet $\underline{Ch}$(OH)), 3.8 (3H singlet OCH$_3$) ppm.

Benzene-ether (4:1 and 2:1) fractions eluted cis-2-($\alpha$-dimethylamino-m-methoxybenzyl)cyclohexanol (10 g.). NMR ($CDCl_3$): $\delta$ 2.12 (6H singlet N($\underline{CH}_3$)$_2$), 3.44–3.66 (2H multiplet $\underline{CH}$(OH) and CH N($\underline{CH}_3$)$_2$), 3.8 (3H singlet —O$\underline{CH}_3$) ppm. The hydrochloride, m.p. 203°–206°, of the trans epimer (19.5 g.) was crystalized from hexane-dichloromethane. Analysis (air dried sample). Found: C, 60.68; H, 9.07; B, 4.53. Calcd. for $C_{16}H_{26}O_2NCl.H_2O$: C, 60.46; H, 8.88; N, 4.41.

The hydrochloride of the cis epimer (8.6 g.), m.p. 205°–208°, was crystallized from methanol-ether. Analysis: C, 64.09; H, 8.74; N, 4.67. Calcd. for $C_{16}H_{26}O_2NCl$ (299.84): C, 64.14; H, 8.98; N, 4.40.

EXAMPLE 3 cis-2-($\alpha$-Dimethylamino-m-Methoxybenzyl)Cyclohexanol Acetate, Hydrochloride Cis-2-($\alpha$-dimethylamino-m-methoxybenzyl)cyclohexanol (3.0 g.), acetic anhydride (5 ml.), and pyridine (15 ml.) were warmed briefly to effect solution and the mixture stood at room temperature overnight. The mixture was poured into dilute NaOH solution and extracted with ether (twice). The ether layers were washed with water (twice) and dried ($K_2CO_3$) then evaporated. Traces of pyridine were removed by azeotropic distillation with toluene to give a crystalline residue. IR 1738, 1615, 1590 cm$^{-1}$. NMR ($CDCl_3$): $\delta$ 1.96 (3H singlet, $\underline{CH}_3$CO·O), 2.06 (6H singlet, N($\underline{CH}_3$)$_2$), 3.38 (2H doublet J = 10.5 cps $\underline{CH}$ NMe$_a$), 3.77 (3H singlet, $\underline{CH}_3$O—), 4.51 (1H multiplet W ½ H 8 cps) ppm.

The thus-formed crystalline acetate was converted directly to the hydrochloride, m.p. 235°–237°, with effervescence. The analytical sample was crystallized from acetone-dichloromethane. Found: C, 63.46; H, 8.46; N, 4.07; Cl, 10.29. Calcd. for $C_{17}H_{26}O_3N$ (327.845): C, 63.24; H, 8.25; N, 4.10; Cl, 10.37.

EXAMPLE 4

Trans-2-($\alpha$-Dimethylamino-m-Methoxybenzyl) Cyclohexanol Acetate

Using the method of Example 3, trans-2-($\alpha$-dimethylamino-m-methoxybenzyl)cyclohexanol was converted to the title compound obtained as a clear oil. IR 1738, 1615, 1590 cm$^{-1}$. NMR ($CDCl_3$): $\delta$ 1.58 (3H singlet, $\underline{CH}_3$CO.O), 2.06 (6H singlet, N($\underline{CH}_3$)$_2$), 3.35

(1H doublet J=9.5 cps CH N(CH$_3$)$_2$), 3.82 (3H singlet CH$_3$O—), 4.65 (1H broad multiplet W ½ H 16 cps) ppm.

EXAMPLE 5

Cis-2-[α-Dimethylamino-m-(Methoxymethoxy)Benzyl]Cyclohexanol and
Trans-2-[α-Dimethylamino-m-(Methoxymethoxy) Benzyl]Cyclohexanol Maleate A solution of m-(methoxymethoxy)benzal cyclohexanone (100 g. 4 × 10$^{-1}$ moles) in ether (100 ml.) was cooled to −5° in a pressure bottle and treated with 50 ml. dimethylamine (7.5 × 10$^{-1}$ moles) and left at room temperature during 60 hours, The reaction mixture was then added dropwise under nitrogen to a stirred suspension of LiAlH$_4$ (20 g.) in ether (1.4 liters) over 1 hour. The reaction mixture was stirred during one further hour and then refluxed during 2 hours. The ice cooled reaction mixture was treated with 3% aqueous NaOH solution (100 ml.) and filtered. The precipitated solids were washed with boiling ether and the combined filtrates evaporated to a volume of about 1 liter. The ether layer was extracted (twice) with an excess of dilute HCl followed by a water extraction. The combined aqueous extracts were back washed with ether basified with ice and 50%HaOH and extracted with ether (twice). The ether layers were washed with brine, dried (K$_2$CO$_3$) and evaporated to an oil (46 g.) shown by glc to consist of two major components. The oil was chromatographed on a Woelm alumina column (1.5 Kg. neutral activity Grade III) built in benzene-hexane 1:1. Benzene-hexane, benzene and early benzene 10% ether fractions eluted 25.8 g. trans-2-[α-dimethylamino-m-methoxymethoxy)benzyl]cyclohexanol. NMR (CDCl$_3$): δ 2.28 (6H singlet, N(CH$_3$)$_2$), 3.0 (1H doublet J=3 cps, CH N(CH$_3$)$_2$), 3.3–3.8 (1H broad multiplet CH OH), 3.48 (3H singlet, OCH$_3$), 5.17 (2H singlet, —OCH$_2$O—) ppm.

Later benzene-ether fractions (9:1 through 1:2) eluted cis-2-[α-dimethylamino-m-(methoxymethoxy)-benzyl]cyclohexanol. NMR (CDCl$_3$): δ 2.1 (6H singlet, N(CH$_3$)$_2$), 3.47 (3H singlet, —OCH$_3$), 3.37–3.7 (Overlapping multiplets CH OH and CH N(CH$_3$)$_2$), 5.21 (2H singlet, —OCH$_2$O—) ppm.

The maleate salt of the trans compound, m.p. 147°–148°, was crystallized from acetone-dichloromethane. NMR (CDCl$_3$): δ 2.97 (6H singlet, N(CH$_3$)$_2$), 3.48 (3H singlet, —OCH$_{,3}$), 3.73 (1H broad multiplet, CH OH), 4.0 (1H singlet, J=3 cps CH N(CH$_3$)$_2$), 5.2 (2H singlet, —OCH$_2$O—), 6.3 (2H singlet, vinylic proton maleate anion), 10.75 (3H broad peak W ½H 24 cps — exchangeable protons). Found: C, 61.59; H, 7.77; N, 3.19. Calcd. for C$_{21}$H$_{31}$NO$_7$ (409.47): C, 61.59; H, 7.63; N, 3.42.

EXAMPLE 6

Trans-2-(α-Dimethylamino-m-Hydrozybenzyl) Cyclohexanol, Maleate

Trans-2-[α-dimethylamino-m-(Methoxymethoxy)-benzyl]cyclohexanol maleate (6 g.) in methanol (150 ml.) was treated dropwise with concentrated HCl until the pH was adjusted to 2. After one hour at reflux the solution was poured onto ice containing an excess of sodium bicarbonate and ammonium hydroxide. The crystalline precipitate (4 g.) was recrystallized to give the analytical sample of the title compound, (free base form) m.p. 220°–225°. NMR(D$_6$MSO): δ 2.2 (6H singlet N(CH$_3$)$_2$). Analysis: Found: C, 72.10; H, 9.43; N, 5.47. Calcd. for C$_{15}$H$_{23}$N$_2$ (249.338): C, 72.25; H, 9.30; N, 5.62.

The maleate salt, m.p. 182°–183° NMR: (D$_6$MSO): (6H singlet N(CH$_3$)$_2$). Found: C, 62.45; H, 7.42; N, 3.82. Calcd. for C$_{19}$H$_{27}$NO$_6$ (365.41): C, 62,45; H, 7.45; N, 3.83.

EXAMPLE 7

Cis-2-(α-Dimethylamino-m-Hydroxybenzyl) Cyclohexanol, Hydrochloride

Cis-2-[α-dimethylamino-m-(Methoxymethoxy)benzyl] cyclohexanol (10 g.) in ether was treated with a slight excess of isopropanolic hydrogen chloride. The gummy solid which crystallized on trituration with boiling ether-acetone was recrystallized first from ethanol-ether and finally from methanol-actone to give the title compound, m.p. 263°–265°. NMR (D$_6$MSO): δ2.47 (6H singlet, N(CH$_3$)$_2$) ppm. Found: C, 63.02; H, 8.65; N, 4.9; Cl, 12.77. Calcd. for C$_{15}$H$_{24}$NO$_2$Cl (285.805): C, 63.03; H, 8.46; N, 4.68; Cl, 12.41.

EXAMPLE 8

Cis-2-(α-Dimethylamino-m-Hydroxybenzyl) Cyclohexanol, N-Oxide

Cis-2-[α-dimethylamino-m-hydroxybenzyl]cyclohexanol (free base 2.59 g. 1.04 × 10$^{-2}$ moles) in tetrahydrofuran (40 ml.) was treated, dropwise at 0°–5° with a solution of m-chloroperbenzoic acid (2.14 g., 85% pure, 1.06 × 10$^{-2}$ moles) in tetrahydrofuran over 30 minutes. The ice bath was removed and after a further 30 minutes the solution was adsorbed onto a basic alumina column (Grade I 100 g.) and eluted with chloroformmethanol (3.1). The eluate crystallized from ethanol-hexane as its hemi-ethanol solvate, m.p. 125°–129° with effervescence.

Found: C, 66.43, H, 9.34; N, 5.21. C$_{15}$H$_{23}$NO$_3$·½C$_2$H$_5$OH requires: C, 66.63; H, 9.09; N, 4.86.

EXAMPLE 9

Cis-2-[α-Dimethylaminobenzyl]-Cyclohexanol and Trans-2-[α-Dimethylaminobenzyl] Cyclohexanol A solution of benzal cyclohexanone (100 g., 5.39 × 10$^{-1}$ moles) in ether (100 ml.) was cooled to −5° in a pressure bottle and treated with 50 ml. dimethylamine (7.5 × 10$^{-1}$ moles) and left at room temperature during 60 hours. The reaction mixture was then added dropwise under nitrogen to a stirred suspension of LiAlH$_4$ (20 g.,) in ether (1.3 liters) over 1 hour. The reaction mixture was stirred during one further hour and then refluxed during 2 hours. The ice cooled reaction mixture was treated with 3% aqueous NaOH solution (100 ml. ) and filtered. The precipitated solids were washed with boiling ether and the combined filtrates evaporated to a volume of about 1 liter. The ether layer was extracted (twice) with an excess of dilute HCl followed by a water extraction. The combined aqueous extracts were back washed with ether basified with ice and 50% NaOH and extracted with ether (twice). The ether layers were washed with brine, dried (K$_2$CO$_3$) and evaporated to an oil (70 g.) shown by g/c to consist of two major components. The oil (60 g.) was chromatographed on a Woelm column (1.8 Kg. neutral activity Grade III) built in benzene-hexane 1:1. Benzene-hexane, benzene and early benzene 10% ether fractions eluted 34.2 g. trans product (free base), m.p. 73°–75°.

NMR (CDCl$_3$): δ 2.27 (6H singlet N(C$\underline{H}_3$)$_2$), 3.05 (1H broad multiplet 3.27–3.74, C$\underline{H}$OH), 4.40 (1H singlet exchangeable -O$\underline{H}$), 7.35 (5H singlet aromatic protons) ppm. Later benzene-ether fractions (4:1 through 3:2) eluted 14 g. of cis product (free base), m.p. 88°–89.5°. NMR (CDCl$_3$): δ 2.07 (6H singlet N(C$\underline{H}_3$)$_2$), 3.51 (narrow multiplet W ½ H 5 cps C$\underline{H}$OH), 3.6 (1H doublet J=10.5 cps, high field peak over laps with CH(OH) Multiplet) ppm. The fumate salt of the trans product was prepared from the free base using fumaric acid in acetone solution, analytical sample m.p. 171°–172° (from acetone-ethanol).

Found: C, 65.40; H, 8.07; N, 4.37. C$_{19}$H$_{27}$NO$_5$ requires: C, 65.31; H, 7.79; N, 4.01.

NMR (DMSO): δ 2.53 (6H singlet N(C$\underline{H}_3$)$_2$), 3.27 (1H broad multiplet C$\underline{H}$OH), 3.77 (1H doublet J=4 cps C$\underline{H}$N(CH$_3$)$_2$, 6.69 (2H singlet, vinylic protons fumarate anion), 7.75 (5H singlet, aromatic protons) ppm.

The hydrochloride salt of the cis compound was prepared from the free base in ether with isopropanolic hydrogen chloride, analytical sample, m.p. 227°–228° (from acetone-dichloromethane).

Found: C, 66.83; H, 9.11; N, 5.49; Cl, 12.9. C$_{15}$H$_{24}$NOCl requires: C, 66.77; H, 8.97; N, 5.19; Cl, 13.4%. NMR (DMSO-D$_2$O exchange) 2.65 (6H singlet NH(C$\underline{H}_3$)$_2$), 3.27 (1H multiplet W ½H 5 cps C$\underline{H}$OH).

EXAMPLE 10

Cis-2-[α-Dimethylamino-m-Methoxybenzyl]Cyclohexanol Propionate, Hydrochloride

A mixture of cis-2-(α-dimethylamino-m-methoxybenzyl) cyclohexanol hydrochloride (3 g.) in pyridine (15 ml.) and propionic anhydride (5ml.) was warmed briefly to effect solution and then stirred at room temperature during 20 hours. The mixture was poured into dilute NaOH solution and extracted with ether (twice). The ether layers were washed with water (twice) and dried (K$_2$CO$_3$) then evaporated. Traces of pyridine were removed by azeotropic distillation with toluene. The residue was chromatographed on a Woelm alumina column (90 g. Grade III neutral) built in hexane-benzene fractions eluted the product in its free base form (1.0 g.) as a colorless oil. The hydrochloride prepared from isopropanolic hydrogen chloride and an ether-hexane solution of the free base had m.p. 226°–228° with effervescence (from acetone-hexane). IR 1730, 1595 cm$^{-1}$.

Found: C, 64.18; H, 8.54; N, 3.82; Cl, 9.68. C$_{19}$H$_{30}$O$_3$NCl requires: C, 64.12; H, 8.50; N, 3.94; Cl, 9.96%. Z

EXAMPLE 11

Cis-2-[α-(Dimethylamino)-m-Hydroxybenzyl] Cyclohexanol, Discetate, Maleate

Cis-2-[α-(dimethylamino)-m-hydroxybenzyl]cyclohexanol, hydrochloride (1.5 g.) acetic anhydride (5 ml.) and pyridine (15 ml.) were warmed briefly to effect solution and then allowed to stand at room temperature overnight. The mixture was poured into dilute NaOh solution and extracted with ether (twice). The ether layers were washed with water (twice) and dried (K$_2$CO$_3$) then evaporated. Traces of pyridine were removed by azeotropic distillation with toluene to give an oily residue which was converted directly into its crystalline maleate salt in acetone. The analytical sample after two recrystallizations from acetone-hexane had m.p. 152°–155°. IR 1765, 1725 cm$^{-1}$.

NMR (CDCl$_3$): δ 2.05 (3H singlet CH$_3$CO), 2.33 (3H singlet CH$_3$CO), 2.7 (6H singlet N(CH$_3$)$_2$H$^+$), 4.3 (1H doublet, J=12 cps CH-N(CH$_3$)$_2$), 4.45 (1H multiplet CH(OAc), 6.3 (2H singlet vinylic protons maleate anion)ppm.

EXAMPLE 12

Cis-2-(α-Dimethylamino-m-Hydroxybenzyl) Cyclohexanol Acetate. Maleate

Cis-2-[α-dimethylamino-m-(Methoxymethoxy)benzyl] cyclohexanol, maleate (1.8 g.) was converted to its free base and acetylated with acetic anhydride (5 ml.) and pyridine (15 ml.) over 48 hours at room temperature. The mixture was poured into dilute NaOH solution and extracted with ether. The ether layers were washed with water (twice), brine, dried (Na$_2$SO$_4$) and evaporated. The residue was azeotroped with toluene to remove traces of pyridine and then treated in acetone solution with a slight excess of isopropanolic hydrogen chloride ( pH <2). After 15 hours, the acetone was removed by evaporation and the residue distributed between ether and dilute NH$_3$ — NaHCO$_3$ solution. The ether extract was washed with brine, dried (Na$_2$SO$_4$) and stripped. The residue was treated with an excess of maleic acid in ethyl acetate and the solvent removed. The residue crystallized (from acetone-hexane) had m.p. 158°–160°.

NMR (CDCl$_3$): δ 2.04 (3H singlet C$\underline{H}_3$CO), 2.7 (6H singlet N(C$\underline{H}_3$)$_2$), 4.14(2H doublet J=10.5 cps C$\underline{H}$N(CH$_3$)$_2$), 4.5 (1H multiplet W ½ H 6 cps C$\underline{H}$ OAc), 6.25 (2H singlet vinylic maleate anion) ppm.

Found: C, 61.77; H, 7.44; N, 3.52. C$_{21}$H$_{29}$NO$_7$ requires: C, 61.90; H, 7.17; N, 3.44%.

EXAMPLE 13

Using methods of Examples 2 and 5 and starting from the requisite benzalcyclohexanone and amine component, the following compounds are obtained:
(Solvent of crystallization in parenthesis)

| Compound | Melting Point |
| --- | --- |
| cis-2-(α-dimethylaminobenzyl) cyclohexanol | free base: 88–89.5° HCl salt: 227–228° (dichloromethane-acetone) |
| trans-2-(α-dimethylaminobenzyl)cyclohexanol | free base: 73–75° fumarate salt: 171–172° (ethanol-acetone) |
| cis-2-[α-dimethylamino-p-(methoxymethoxy)benzyl] cyclohexane | fumarate salt: 167–168° (hemiacetonate) (acetone-hexane) |
| trans-2-[α-dimethylamino-p-(methoxymethoxy)benzyl] | maleate salt: 125–127° (ethyl acetate-hexane) |

-continued

| Compound | Melting Point |
| --- | --- |
| cyclohexane | |
| cis-2-(m-chloro-α-dimethylaminobenzyl)cyclohexanol | hydrochloride salt: 140–145° (isomer mixture) (ether) |
| trans-2-(m-chloro-α-dimethylaminobenzyl)cyclohexanol | hydrochloride salt: 207–208° (isomer mixture) (CH$_2$Cl$_2$-ether) |
| cis-2-[α-(ethylmethylamino)-m-(methoxymethoxy)benzyl]cyclohexanol | fumarate salt: 155–157° (methanol-ether) |
| trans-2-[α-(ethylmethylamino)-m-(methoxymethoxy)benzyl]cyclohexanol | maleate salt: 138–140° (methanol-ether) |
| cis-2-[m-methoxymethoxy-α(1-pyrrolidinyl)benzyl]cyclohexanol | fumarate salt: 149–150° |
| trans-2-[m-methoxymethoxy-α(1-pyrrolidinyl)benzyl]cyclohexanol | maleate salt: 117–118° |
| cis-2-[m-methoxymethoxy-α-morpholinobenzyl)cyclohexanol | fumarate salt: 170–172° |
| trans-2-[m-methoxymethoxy-α-morpholinobenzyl)cyclohexanol | maleate salt: 126–127° |
| cis-2-(α-dimethylamino-o-methoxymethoxybenzyl)cyclohexanol | maleate: 125–126° (methanol-ether) |
| trans-2-(α-dimethylamino-o-methoxymethoxybenzyl)cyclohexanol | maleate: 134–135° (methanol-ether) |
| cis-2-[α-(benzylmethylamino)-m-(methoxymethoxy)benzyl]cyclohexanol | |
| trans-2-[α-(benzylmethylamino)-m-(methoxymethoxy)benzyl]cyclohexanol | |
| cis-2-(p-chloro-α-dimethylaminobenzyl)cyclohexanol | hydrochloride: 230–232° (ethanol) (mixture of isomers) (ethanol-ether) |
| trans-2-(p-chloro-α-dimethylaminobenzyl)cyclohexanol | hydrochloride: 120–125° (methanol) (mixture of isomers) (methanol-ether) |

EXAMPLE 14

Cis-2-(α-Dimethylamino-m-Hydroxybenzyl) Cyclohexanol, Hydrochloride

Cis-2-[α-dimethylamino -m-(Methoxymethoxy)benzyl] cyclohexanol (260 g.) as a suspension in tetrahydrofuran (1.5 l.) was treated with isopropanolic hydrogen chloride (300 ml. 4.65N). A clear solution was immediately obtained from which the crystalline title compound (230 g.) separated overnight.

EXAMPLE 15

Using the methods of examples 6 and 7 and starting from the appropriate methoxymethyl ethers in following compounds are obtained:

| Compound | Melting Point |
| --- | --- |
| cis-2-(α-dimethylamino-p-hydroxybenzyl)cyclohexanol | hydrochloride salt (½ H$_2$O): 159–163°(ether) |
| trans-2-(α-dimethylamino-p-hydroxybenzyl)cyclohexanol | hydrochloride salt (½ H$_2$O): 130– °(ether) |
| cis-2-[α-(ethylmethylamino)-m-hydroxybenzyl]cyclohexanol | hydrochloride salt (hemihydrate) 85° with effervescence (ether) |
| trans-2-[α-(ethylmethylamino)-m-hydroxybenzyl]cyclohexanol | hydrochloride salt (hemihydrate): 85–90° with effervescence (ether) |
| cis-[m-hydroxy-α-(1-pyrrolidinyl)benzyl]cyclohexanol | hydrochloride salt: 238° with effervescence (methanol-ether) |
| trans-[m-hydroxy-α-(1-pyrrolidinyl)benzyl]cyclohexanol | fumarate salt: 227° with effervescence (methanol-ether) |
| cis-2-(m-hydroxy-α-morpholinobenzyl)cyclohexanol | hydrochloride salt: 247° effervescence (ethanol) |
| trans-2-(m-hydroxy-α-morpholinobenzyl)cyclohexanol | fumarate salt: 230° effervescence (methanol) |
| cis-2-[α-dimethylamino-o-hydroxybenzyl]cyclohexanol | maleate salt: 145–146° (ethyl acetate) |
| trans-2-[α-dimethylamino-o-hydroxybenzyl]cyclohexanol | maleate salt: 150–151° (ethyl acetate-ether) |
| cis-2-[α-(benzylmethylamino)-m-hydroxybenzyl]cyclohexanol | hydrochloride (.H$_2$O) salt: 239–240° with effervescence (tetrahydrofuran) |
| trans-2-[α-benzylmethylamino)-m-hydroxybenzyl]cyclohexanol | free base: 207–209° (acetone-tetrahydrofuran) |
| cis-2-[m-hydroxy-α-(methylamino)benzyl]cyclohexanol | hydrochloride salt: 263–265° effervescence (methanol-acetone) |
| trans-2-[m-hydroxy-α-methyl- | hydrochloride salt: 232–232.5° |

| Compound | Melting Point |
|---|---|
| amino)benzyl]cyclohexanol | (methanol-ether) |

EXAMPLE 16

Cis-2-[m-Methoxymethoxy-α-(Methylamino) Benzyl]Cyclohexanol

A mixture of cis-2-[α-(benzylmethylamino)-m-(methoxymethoxy) benzyl]cyclohexanol (24.6 g., 6.68 × $10^{-2}$ moles), methanol (300 ml.), 10% Pd on C (4 g.) and acetic acid (5 ml. glacial, 8.75 × $10^{-2}$ moles) was hydrogenated at room temperature using a hydrogen pressure of 20 –45 p.s.i. After filtration from the catalyst the reaction mixture was concentrated in vacuo and the residue distributed between ether and excess NaOH solution. The ether was washed with brine, dried ($Na_2SO_4$) and evaporated. Crystallization of the residue from ethertetrahydrofuran afforded the product (12 g.), m.p. 87°–89°/ NMR ($CDCl_3$): δ 2.27 (3H singlet NHC$\underline{H}_3$), 3.45 (3H singlet, OC$\underline{H}_3$), 3.72 (1H apparent singlet W½H 3 cps), 4.15 (1H multiplet W½H6 cps), 5.12 (2H singlet, —OC$H_2$O—) ppm.

Found: C, 68.98; H, 9.21; N. 4.88. $C_{16}H_{25}NO_3$ requires: C, 68.78; H, 9.02; N. 5.01%.

Maleate salt, m.p. 152°–154° (acetaone:hexane).

Found: C, 60.98; H, 7.41; N, 3.48. $C_{16}H_{25}NO_3·C_4H_4O_4$ requires: C, 60.74; H, 7.39; N, 3.54.

Trans-2-[m-methoxymethoxy-α-(methylamino)benzyl]cyclohexanol, fumarate salt (1.5 moles fumaric acid per mole compound), m.p. 147°–148° (methanol-ether), was similarly prepared by the above method.

EXAMPLE 17

Using the process of Example 16. but replacing acetic acid by hydrochloric acid (since no acid-labile methoxymethoxy group is present), there were prepared trans-2-[m-hydroxy-α-(methylamino)benzyl]cyclohexanol hydrochloride, m.p. 232°–232.5° (acetone), and cis-2-[m:hydroxy-α-(methylamino)benzyl]cyclohexanol hydrochloride, m.p. 263°–265° (methanol-ether).

EXAMPLE 18

Cis-2-[m-Methoxy-α-(Methylamino) Cyclohexanol

Cis-2-[m-hydroxy-α-(methylamino)benzyl]cyclohexanol, hydrochloride (1 g.) in methanol was treated with an excess of ethereal diazomethane during 2 days at room temperature. The solution was evaporated and the residue distributed between ether and dilute NaOH solution. The ether extract was washed with brine, dried ($Na_2SO_4$) and treated with isopropanolic HCl to give the product as its hydrochloride, m.p. 222°–223° (methanol-ether).

Found: C, 63.05; H, 8.45; N, 5.01; Cl, 12.57. $C_{15}H_{23}NO_2$·Hcl requires: C, 63.03; H, 8.46; N, 4.9; Cl, 12.41.

In similar manner trans-2-[methoxy-α-(methylamino) benzyl]cyclohexanol, fumarate, m.p. 142°–155° (hemihydrate from acetone) was obtained.

EXAMPLE 19 d-CIS-2-(α-Dimethylamino-m-Hydroxybenzyl) Cyclohexanol and 1-Cis-2-(α-Dimethylamino-m-Hydroxybenzyl)Cyclohexanol A warm solution of 2R:3R tartaric acid (7.5 g., 5 × $10^{-2}$ moles) and cis-2-(α-dimethylamino-m-hydroxybenzyl)cyclohexanol (12 g., 4.82 × $20^{-2}$ moles) in ethanol (100 ml.) was diluted with boiling acetone to a final volume of 900 ml. filtered to clarify the solution, seeded with positive rotating isomer and kept at ca. 25° during 20 hours. The crystalline solid (7 g.) that separates is twice recrystallized from ethanol-acetone to give d-cis-2-(α-dimethylamino-m-hydroxybenzyl)cyclohexanol, 2R:3R-tartrate (mono) acetone solvate (4.9 g.), m.p. 198°–200°, $[\alpha]_D^{25}$ + 45.53 (c 1.05, McOH). NMR indicates that the product is a partial acetone solvate even after extensive drying.

A solution (3.7 g.) of the preceding salt in water is basified with a 1:1 mixture of saturated $NaHCO_3$ solution and concentrated $NH_4OH$ and the base is extracted (twice) with ether. The ether extracts are washed with brine and dried ($Na_2SO_4$). Removal of the solvent affords a crystalline solid (1.89 g.). Recrystallization of a portion from acetone-hexane affords the analytical sample, m.p. 191°–193°, $[\alpha]_D^{25}$ + 45.21 (c 1.074 MeOH) of d-cis-2-(α-dimethylamino-m-hydroxybenzyl)cyclohexanol.

Found: C, 72.28; H, 9.40; N, 5.58. $C_{15}H_{23}NO_2$ requires: C, 72.25; H, 9.30; N, 5.62%.

The hydrochloride, m.p. 255°–257° effervescence, $[\alpha]_D^{25}$ + 14.70 (c, 1.045 MeOH) was obtained by treatment of the base in ether with isopropanolic hydrogen chloride and trituration of the precipitate with boiling acetone until heavily crystalline. Found: C, 62.66; H, 8.46; N, 4.92; Cl, 12.52. $C_{15}H_{23}NO_2$.HCl requires: C, 63.03; H, 8.46; N, 4.9; Cl, 12.41%.

A portion reconverted to the free base had $[\alpha]_D^{25}$ + 43.3 indicating no racemization had occurred.

The acetone-ethanol filtrates remaining after separation of the 2R:3R tartrates are combined, freed of solvent and the residue distributed between ether and a saturated $NaHCO_3$ solution, concentrated $NH_4OH$ mixture. The aqueous extract was washed with ether (twice) and the combined ether extracts washed with brine, dried ($Na_2SO_4$) and freed of solvent. A solution of the residue (6.0 g., 2.4 × $10^{-2}$ moles) in warm ethanol (100 ml.) was treated with 2S:3S tartaric acid (3.75 g., 2.49 × $10^{-2}$ moles) and diluted with boiling acetone (900 ml.), filtered and stood at 25° during 60 hours. The crystalline solid (6.8 g.) that separates is twice crystallized from ethanol-acetone to give 1-cis-2-(α-dimethylamino-m-hydroxybenzyl) cyclohexanol, 2S:3S-tartrate (mono) acetone solvate 4.5 g., m.p. 198°–200°, $[\alpha]_D^{25}$ − 45.70° (c, 0.965 MeOH).

A solution of 3.7 g. of the preceding salt in water is basified with a 1:1 mixture of saturated $NaHCO_3$ solution and concentrated $NH_4OH$ and the base is extracted (twice) with ether. The ether extracts are washed with brine and dried ($Na_2SO_4$). Removal of the solvent affords a crystalline residue (1.75 g.). Recrystallization of a portion from acetone-hexane affords the analytical sample, m.p. 191°–193°, $[\alpha]_D^{25}$ − 46.92° (c, 1.061 MeOH) of 1-cis-2-($\alpha$-dimethylamino-m-hydroxybenzyl)cyclohexanol.

Found: C, 72.54; N, 9.37; N, 9.37; N, 5.68. $C_{15}H_{23}NO_2$ requires: C, 72.25; H, 9.30; N, 5.62%.

The hydrochloride, m.p. 255°–257° effervescence $[\alpha]_D^{25}$ − 15.31°(c, 1.067 MeOH) was obtained by treatment of the base in ether with isopropanolic HCl and trituration of the precipitate with boiling acetone.

Found: C, 62.90; H, 8.57; N, 4.93; Cl, 12.00. $C_{15}H_{23}NO_2 \cdot HCl$ requires: C, 63.03; H, 8.46; N, 4.90; Cl, 12.41%.

A portion reconverted to the free base had $[\alpha]_D^{25}$ − 45.86° indicating no racemization had occurred.

EXAMPLE 20

Octahydro-3-(m-Methoxyphenyl)-2-Methyl-1,2-Benzisoxazole

C-(m-methoxyphenyl)-N-methyl nitrone (16.5 g., $10^{-1}$ mole) and cyclohexene (120 ml., 1.3 moles) were heated in a 250 ml. capacity Parr bomb at 150° during 40 hours. Cyclohexene was removed from the crude reaction mixture under reduced pressure and the residue in ether washed with water to remove any unchanged nitrone. The organic layer was extracted (thrice) with dilute HCl, the aqueous extracts washed with ether and basified strongly with NaOH solution and re-extracted (twice) with ether. The ether layer was washed with water, dried ($Na_2SO_4$) and evaporated to give the product as a pale straw colored oil (86% pure by glc). The product was characterized as its hydrochloride obtained as a hemiacetone solvate, m.p. 140°–142° with effervescence from acetone solution. Found: C, 63.72; H, 8.11; N, 4.67; Cl, 11.33. $C_{15}H_{22}NO_2Cl \cdot \frac{1}{2}(CH_3COCH_3)$ requires: C, 63.35; H, 8.06; N, 4.48; Cl, 11.55%.

EXAMPLE 21

Following the procedure of example 20, the following compounds were prepared:

EXAMPLE 22

Octahydro-3-(m-Methoxyphenyl)-2,2-Dimethyl-1,2-Benzisoxazolium Iodide

Crude octahydro-3-(m-methoxyphenyl)-2-methyl-1,2-benzisoxazole (15 g.) in tetrahydrofuran (120 ml.) was treated with an excess of methyl iodide (15 ml.). A crystalline solid began to separate almost immediately. After 12 hours the precipitate was filtered and washed with tetrahydrofuran to give the analytically pure product, m.p. 165° with decomposition.

Found: C, 49.32; H, 6.28; N, 3.63; I, 32.98. $C_{16}H_{24}NO_2I$ requires: C, 49.36; H, 6.21; N, 3.60; I, 32.60%.

The following compounds were prepared by the above method; m.p. and solvent of crystallization are indicated:

| | |
|---|---|
| Octahydro-3-(m-methoxymethoxyphenyl)-2,2-dimethyl-1,2-benzisoxazolium iodide | m.p. 150° decomp. (methanol-ether) |
| Octahydro-2,2-dimethyl-3-phenyl-1,2-benzisoxazolium iodide | m.p. 164° decomp. (methanol-ether) |
| Hexahydro-3-(m-methoxymethoxyphenyl)-2,2-dimethyl-2H-cyclopentyl[$\alpha$]isoxazolium iodide | m.p. 152° decomp. (methanol-ether) |

EXAMPLE 23

Epi-Cis-2-($\alpha$-Dimethylamino-m-Methoxybenzyl)Cyclohexanol, Hydrochloride

Octahydro-3-(m-methoxyphenyl)-2,2-dimethyl-1,2-benzisoxazolium iodide (10 g.) and anhydrous sodium acetate (5 g.) in absolute ethanol (150 ml.) were hydrogenated using a Raney nickel catalyst. Rapid uptake of 0.85 equivalents hydrogen was observed over 25 minutes. No further significant absorption occurred after a further 50 minutes. The reaction mixture was evaporated under reduced pressure and the residue distributed between ether and dilute NaOH solution. The ether extract was washed with brine, dried ($Na_2SO_4$) and treated with isopropanolic hydrogen chloride to give after crystallization from acetone the product (4.5 g.), m.p. 219°–222°. NMR ($CDCl_3$-$D_2O$): δ 2.77 (6H singlet, $^+NMe_2$), 3.9 (3H singlet, —$OCH_3$), 4.34 (1H doublet J=11 cps, —C$\underline{H}$NMe$_2$), 4.5 (1H multiplet W½H 9 cps) ppm.

Found: C, 64.17; H, 8.97; N, 4.71. $C_{16}H_{26}NO_2Cl$ requires: C, 64.09; H, 8.74; N, 4.67%.

The following compounds were prepared by the above method; m.p. and recrystallization solvent data are included.

| | nmr ($CDCl_3$) N—$CH_3$ |
|---|---|
| Octahydro-2-(m-methoxymethoxyphenyl)-2-methyl-1,2-benzisoxazole | 2.72 |
| Octahydro-2-methyl-3-phenyl-1,2-benzisoxazole | 2.70 |
| Hexahydro-3-(m-methoxymethoxyphenyl)-2-methyl-2H-cyclopent[d]isoxazole | 2.5 |
| Octahydro-3-(m-methoxymethoxyphenyl)-2-methyl-2H-cyclohept[d]isoxazole (2 comp. 62% and 38% mixture by glc) | 2.5; 2.66 |
| Decahydro-3-(m-methoxymethoxyphenyl)-2-methylcyclooct[d]isoxazole (2 comp. 47% and 53% mixture by glc) | 2.5; 2.67 |

| | |
|---|---|
| epi-cis-2-[α-dimethylamino-m-(methoxymethoxy)benzyl]cyclohexanol fumarate | m.p. 156–157° (acetone-hexane) |
| epi-cis-2-(α-dimethylaminobenzyl)cyclohexanol, hydrochloride | m.p. 195–196° (acetone-hexane) free base, m.p. 111–113° (hexane) |
| epi-cis-2-(α-dimethylamino-m-(methoxymethoxy)benzyl]cyclohexanol fumarate | m.p. 120–124° (acetone-hexane) |

EXAMPLE 24 epi-cis-2-(α-Dimethylamino-m-Hydroxybenzyl)Cyclohexanol epi-cis-2-[α-dimethylamino-m-(methoxymethoxy)-benzyl] cyclohexanol fumarate (5 g.) in tetrahydrofuran (120 ml.) was treated with 2 ml. of concentrated hydrochloric acid (pH solution 2) allowed to stand overnight at room temperature. The mixture was concentrated in vacuo at temperatures <30° and diluted with sodium bicarbonate-ammonium hydroxide mixture. The product obtained by extraction with chloroform was recrystallized from ether-hexane to give an analytical sample (2.7 g.), m.p 172°–173.5°. NMR (CDCl$_3$): δ 2.17 (6H singlet N(CH$_3$)$_2$), 4.05 (2H overlapping 1H doublet J=12 cps CHN(Me$_2$) and 1H multiplet CH OH), 8.4 (2H exchangeable protons phenolic and alicyclic hydroxyls) ppm.

Found: C, 72.19; H, 9.68; N, 5.54. C$_{15}$H$_{23}$NO$_2$ requires: C, 72.25; H, 9.30; N, 5.62.

The hydrochloride, m.p. 241°–242° with effervescence, crystallized from an acetone-ethanol-hexane mixture.

Found: C, 63.02; H, 8.65; N, 4.68; Cl, 12.77. C$_{15}$H$_{24}$NO$_2$Cl requires: C, 63.03; H, 8.46; N, 4.9; Cl, 12.41%.

EXAMPLE 25

Following the procedure of example 24, there was prepared epi-cis-2-(α-dimethylamino-m-hydroxybenzyl)cyclopentanol, m.p. 172°–173° (acetone-hexane). The hydrochloride of this compound had a melting point of 201°–202° (ethanol-hexane).

EXAMPLE 26 epi-cis-2-(α-Dimethylamino-m-Hydroxybenzyl)Cyclohexanol-N-Oxide

Epi-cis-2-(α-dimethylamino-m-hydroxybenzyl)cyclohexanol (2.06 g., 8.3 × 10$^{-3}$ moles) in tetrahydrofuran (25 ml.) was cooled to 0° and treated dropwise during 45 minutes with m-chloroperbenzoic acid (1.74 g., 8.4 × 10$^{-3}$ moles) in tetrahydrofuran (18 ml.). The reaction mixture was allowed to reach room temperature for over 1 hour and then filtered through a Woelm alumina column (Grade I, basic 100 g.) and eluted with chloroform-methanol (3:1). The eluate crystallized from ethanol-hexane to give the product (1.2 g.), m.p. 147°–148°.

Found: C, 68.21; H, 9.38; N, 4.78, 4.99. C$_{15}$H$_{23}$NO$_3$ requires: C, 67.89; H, 8.74; N, 5.08%.

EXAMPLE 27 epi-cis-2-(α-Dimethylamino-m-Methoxybenzyl)Cyclohexanol Acetate

Epi-cis-2-(α-dimethylamino-m-methoxybenzyl)cyclohexanol (1.5 g.) acetic anhydride (3 ml.) and pyridine (10 ml.) were warmed briefly to effect solution. The mixture was poured into dilute NaOH solution and extracted with ether. The ether layers were washed with water (twice) and dried (K$_2$CO$_3$) then evaporated. Traces of pyridine were removed by azeotropic distillation with toluene to give the product as a colorless oil. IR 1730 cm$^{-1}$. NMR (CDCl$_3$): δ 2.04, 2.06 (2 singlets (9H)-N(CH$_3$)$_2$ and OCOCH$_3$), 3.32 (1H doublet J=10.5 cps CHN(CH$_3$)$_2$), 3.8 (3H singlet —OCH$_3$), 5.43 (1H multiplet, W½H 7 cps, —CH—OCOCH$_3$) ppm.

EXAMPLE 28

An injectable unit dosage composition is prepared by dissolving 1 g. of cis2-(α-dimethylamino-m-hydroxybenzyl)cyclohexanol, hydrochloride in 50 ml. of 0.1 M phosphate buffer, pH 7.4, and making it up to 100 ml. with distilled water. This solution of medicament, containing 10 mg/ml of active ingredient, is subjected to sterile filtration through a 0.45 micron filter, and 1 ml. aliquots are filled aseptically into sterile ampules. The ampules are flame sealed and the contents are frozen and stored at −20° C. until needed.

EXAMPLE 29

Tablets for oral use are prepared with the following formulations:

| | Milligrams | |
|---|---|---|
| cis-2-(α-dimethylamino-m-hydroxybenzyl)cyclohexanol, hydrochloride | 10 | 15 |
| lactose | 287 | 282 |
| magnesium stearate | 3 | 3 |
| | 300 | 300 |

EXAMPLE 30

Cis-2-(α-Dimethylamino-m-Ethoxybenzyl)Cyclohexanol, Maleate

A mixture of cis-2-(α-dimethylamino-m-hydroxybenzyl) cyclohexanol (6.6 g., 2.5 × 10$^{-2}$ moles) and powdered K$_2$CO$_3$ (10 g., 7.2 × 10$^{-2}$ moles) in warm ethanol (30 ml.) was treated with a solution of ethyl iodide (2.2 ml., 4.3 g., 2.75 × 10$^{02}$ moles) in ethanol (15 ml.) added, dropwise, over 20 minutes. The reaction mixture was refluxed for 90 minutes, evaporated and the residue distributed between ether and water (pH aqueous phase 11–12), the ether layer was washed with water, brine and dried (Na$_2$SO$_4$). Evaporation of the ether afforded an oily residue which was characterized as its maleate salt, m.p. 166°–7° (from ethanol-ether).

Found: C, 64.19; H, 7.94; N, 3.63. $C_{21}H_{31}NO_6$ requires: C, 64.10; H, 7.94; N, 3.56%.

EXAMPLE 31

Cis-2-Methoxy-α-(m-Methoxymethoxyphenyl)-N.N-Dimethylcyclohexanemethylamine Maleate and α-Dimethylamino-α-(Cis-2-Methoxycyclohexyl)-m-Cresol, Hydrochloride Cis-2-[α-(dimethylamino)-m-(methoxymethoxy)-benzyl] cyclohexanol (5.9 g., 0.02 moles) in tetrahydrofuran (100 ml.) was treated at room temperature and in a nitrogen atmosphere, with 1.6 molar butyl lithium (12.5 ml., 0.02 moles) during 1 hr. The mixture was cooled to −70° and treated over 30 minutes with a solution of methyl iodide (1.25 ml., 0.02 moles) in tetrahydrofuran. The reaction mixture was stirred at room temperature during 48 hours. Methanol (5 ml.) was added and the reaction mixture evaporated and the residue, in ether, was washed with water, brine and dried ($Na_2SO_4$), the product (4.0 g.) was purified by descending column chromatography on alumina using $CH_2Cl_2$ to develop the column. 1.0 g. was converted to the maleate, cis-2-methoxy-α-(m-methoxymethoxyphenyl)-N,N-dimethylcyclohexanemethylamine, maleate, m.p. 112°–115°, NMR ($CDCl_3$): δ3.0 (3H singlet $OCH_3$), 4.45 (1H doublet J=10.5 cps $CHN(CH_3)_2$) ppm.

Found: C, 62.47; H, 7.92; N, 3.29. $C_{22}H_{33}NO_7$ requires: C, 62.39; H, 7.85; N, 3.30%. Treatment of the free base in tetrahydrofuran with dilute HCl afforded α-dimethylamino-α-(cis-2-methoxycyclohexyl)-m-cresol, hydrochloride, m.p. 227°–228° (from ethanol-ether).

Found: C, 63.25; H, 9.17; N, 4.25; Cl, 11.53. $C_{16}H_{26}NO_2Cl.¼H_2O$ requires: C, 63.15; H, 8.83; N, 4.60; Cl, 11.65%.

EXAMPLE 32 d-Cis-2-(α-Dimethylaminobenzyl)Cyclohexanol and l-Cis-2-(α-Dimethylaminobenzyl)Cyclohexanol A warm solution of cis-2-(α-dimethylaminobenzyl)-cyclohexanol (38.16 g., 0.167 moles) and l-malic acid (22.8 g., 0.17 m.) in methanol (200 ml.) was diluted with 600 ml. ether and the crystalline precipitate recrystallized to constant optical rotation (5 times from methanol-ether) to give d-cis- 2-(α-dimethylaminobenzyl)cyclohexanol, l-malate (15 g.), m.p. 195°–196°, $[α]_D^{25}$ + 15.2 (C, 1.006 MeOH).

Found: C, 62.44; H, 8.43; N, 3.98. $C_{19}H_{29}NO_6$ requires: C, 62.11; H, 7.96; N, 3.82%.

A portion reconverted to the free base had $[α]_D^{25}$ + 53.2 (C, 1.057 MeOH).

The filtrates from the l-malate recrystallizations were stirred in water and ether and basified with NaOH, extracted, washed, dried and evaporated to give 28.0 g. residue which was dissolved with d-malic acid (17 g.) in hot methanol (200 ml.) and diluted with ether (600 ml.). The crystalline precipitate was recrystallized three times from methanol/ether to give l-cis-2-(α-dimethylaminobenzyl)cyclohexanol, d-malate, m.p. 195.5°–196.5°, $[α]_D^{25}$ − 15.8 (C, 0.9095 MeOH).

A portion reconverted to the free base had $[α]_D^{25}$ − 53.6 (C, 1.049 MeOH).

EXAMPLE 33

Cis-2-[m-Hydroxy-α(Methyl(3-Methyl-2-butenyl)Amino]Benzyl]Cyclohexanol, Hydrochloride Cis-2-(m-methoxymethoxy-α-(Methylamino)Benzyl]Cyclohexanol(2.5 g., 8.95 × $10^{-3}$ moles), sodium bicarbonate (1.2 g., 1.43 × $10^{-2}$ moles) and 1-chloro-3-methyl-2-butene (1.05 g., 1 × $10^{-2}$ moles) in DMF (40 ml.) were refluxed with stirring during 4 hours. The reaction mixture was stripped and the organic residue treated overnight in THF (30 ml.) with isopropanolic hydrogen chloride (2.5 ml.). The crystalline precipitate was recrystallized from acetone to give the product, m.p. 202°–203° with effervescence.

Found: C, 66.72; H, 9.15; N, 3.97. $C_{19}H_{29}NO_2.HCl$ requires: C, 67.14; H, 8.90; N, 4.12%.

EXAMPLE 34

Cis-2-(α-Dimethylaminobenzyl)Cyclohexanol, Epi-Cis-2-(α-Dimethylaminobenzyl)Cyclohexanol, Trans-2-(α-Dimethylaminobenzyl)Cyclohexanol and Epi-Trans-2-(α-Dimethylaminobenzyl)Cyclohexanol A solution of benzalcyclohexanone (68 g.) in ether (80 ml.) containing dimethylamine (36 ml.) was stored in a Parr bomb during 1 month after which the total reaction mixture was reduced with excess $LiAlH_4$ and the product worked up exactly as described for Example 9. The oily product (47 g.) was absorbed onto alumina (200 g.) and added to a column of alumina (1.8 kg. Woelm Grade III neutral) and eluted initially with hexane fractions containing increasing amounts of benzene. Later fractions were of benzene and benzene containing increasing amounts of ether. The compounds were eluted in the order: trans, (hexane-benzene fractions), epi-trans (benzene fractions), epi-cis, and cis-2-[α-dimethylaminobenzyl]cyclohexanol (benzene-ether fractions). The cis- and trans- forms were identical with the products of example 9, the epi-cis form with that obtained in Example 23. The epi-trans fraction (12.8 g.) was heated with a slight excess of fumaric acid in acetone to give a crystalline precipitate of the fumarate salt, m.p. 177°–180° (from ethanol) NMR (DMSO): δ 2.48 (6H singlet, $Nh(CH_3)_2)^+$ 3.35 (1H broad multiplet, CH(OH)) 4.23 (1H doublet J=8 cps, CH $N(CH_3)_2$) ppm.

Found: C, 65.75; H, 8.08; N, 3.93. $C_{19}H_{27}NO_5$ requires: C, 65.31; H, 7.79; N, 4.01%.

EXAMPLE 35

Cis-2-[α-(cyclopropylmethyl)Methylamino-m-Hydroxybenzyl]Cyclohexanol, Hydrochloride Cis-2-[m-methoxymethoxy-α-(methylamino)benzyl]cyclohexanol (2.5 g., 8.95 × $10^{-3}$ moles) and cyclopropanecarboxylic acid chloride (2.0 g., 1.91 × $10^{-2}$ moles) was stirred in a two phase system consisting of 10% $K_2CO_3$ solution (100 ml.) and $CH_2Cl_2$ (60 ml.). After 6 hours the organic layer was separated and evaporated to give a colorless oil which was refluxed in THF-ether (120 ml., 1:1) with $LiAlH_4$ (1.0 g.) overnight. The ice-cooled reaction mixture was treated with 5 ml. 3% NaOH and filtered. The organic layer was evaporated and the residue in THF (15 ml.) treated with ethanolic hydrogen chloride (5 ml.), the product (1.7 g.) crystallized overnight, m.p. 228° effervescence (from methanol-ether).

Found: C, 66.69; H, 8.71; N, 4.11; $C_{18}H_{27}NO_2 \cdot HCl$ requires: C, 66.34; H, 8.66; N, 4.30.

EXAMPLE 36

Epi-Cis-2-[m-Methoxymethoxy-$\alpha$-(Methylamino)-Benzyl]Cyclohexanol

Octahydro-2-(m-methoxymethoxphenyl)-2-methyl-1,2-benzisoxazole (14 g., .05 moles) in ethanol (150 ml.) was shaken with Raney nickel in a hydrogen atmosphere at 33 p.s.i. overnight. A total uptake of 0.058 moles hydrogen was observed. After filtration from catalyst the solvent was evaporated and the residue subjected to descending column chromatography on an alumina column developed with chloroform. Two major components were obtained. One a non-basic relatively non-polar component was rejected. The second component was isolated as its crystalline fumarate, 6.2 g., m.p. 155°–161° (from methanol-ether) NMR ($D_6MSO$): δ 2.27 (3H singlet $NHCH_3$) ppm.

Found: C, 60.03; H, 7.38; N, 3.39. $C_{16}H_{25}NO_3 \cdot C_4H_4O_4$ requires: C, 60.75; H, 7.39; N, 3.55%.

EXAMPLE 37

Cis-2-($\alpha$-Dimethylamino-m-Hydroxybenzyl)Cyclohexanol m-Methoxymethoxybenzalcyclohexanone (30 g., $1.21 \times 10^{-1}$ moles) in ether (40 ml.) was heated with dimethylamine (25 ml., $\times 10^{-1}$ moles) in a pressure bomb for 2 days. at room temperature. The solvents were removed in vacuo, the residue diluted with ether (100 ml.), and the solvents again removed in vacuo to remove last traces of dimethylamine. The residue in THF (60 ml.) was added durng 40 minutes to a stirred 1 molar solution of tetrahydrofuran-borane (150 ml., $1.5 \times 10^{-1}$ moles) under an atmosphere of nitrogen. The reaction mixture was maintained in the range 0°–10° during the addition. The reaction mixture was allowed to reach room temperature during 2 hours, then cooled to −10° before treatment with 10% aqueous-tetrahydrofuran (8.1 ml. $H_2O$ ($4.5 \times 10^{-1}$ moles), 81 ml. THF ) followed by 35 ml. 4.3N isopropanoilic hydrogen chloride. Slow evolution of hydrogen in a mild exothermic reaction characterized the decomposition of inermediate amine-boranes. After seeding with cis-2-($\alpha$-dimethylamino-m-hydroxbenzyl)cyclohexanol, hydrochloride, slow crystallization of the product (19.5 g.) occurs. The hydrochloride was dissolved in water and treated with excess $NH_4OH$ and $NaHCO_3$ solution and the generated free base extracted into ether. The ether extracts were evaporated and triturated with hexane containing small amounts of THF to give cis-2-($\alpha$-dimethylamino-m-hydroxybenzyl)cyclohexanol (15 g.), m.p. 142°.

EXAMPLE 38

Using the method of Example 1 cycloheptanone and the appropriate aldehyde were converted into:
1. m-methoxymethoxybenzalcycloheptanone, b.p. 175° at 0.8 mm.
2. benzalcycloheptanone; b.p. 137–143° at 0.8–0.9 mm.

EXAMPLE 39

Using the method of Example 5 the following compounds were obtained from the appropriate benzylidene compound and dimethylamine:

1. cis-2-[$\alpha$-dimethylamino-m-(methoxymethoxy)-benzyl] cycloheptanol maleate, m.p. 123°–125° (from ethylacetate-ether).
2. cis-2-[$\alpha$-dimethylaminobenzyl]cycloheptanol hydrochloride, m.p. 159°–160° (from isopropanol ether)

EXAMPLE 40

Cis-2-($\alpha$-Dimethylamino-m-Hydroxybenzyl)-1-Methylcyclohexanol Fumarate

A solution of m-(methoxymethoxy)benzal cyclohexanone (100 g.); $4 \times 10^{-1}$ moles in ether (100 ml.) was cooled to −5° in a pressure bottle and treated with dimethylamine (100 ml.) and left at room temperature overnight. The reaction mixture was evaporated and the residue dissolved in ether was washed with water (2 times, discarded) and extracted with dilute HCl (two times) and water. The combined acid extracts were washed with ether and then basified with ice cold NaOH. Extraction with eher afforded 96.5 g. of the dimethylamino adduct (I.R. SAT C=O peak only). The adduct (96 g.) in ether (400 ml.) was added to a 3 molar solution of methylmagnesium bromide in ether (250 ml.) over 30 minutes, refluxed during 90 minutes and finally allowed to stand at room temperature overnight. Afte treatment with 75 ml. ice-cold saturated $NH_4Cl$ solution, basic material (50 g.) was isolated exactly as described for the dimethylamino adduct and chromatographed on alumina (1.7 kg., Woelm, Grade III, neutral). Benzene-hexane (1:2) and benzene fractions eluted trans-2-($\alpha$-dimethylamino-m-methoxymethoxybenzyl)-1-methylcyclohexanol (I) as an oil NMR ($CDCl_3$): δ 2.05 (6H singlet, $N(CH_3)_2$), 1.12 (3H singlet $CH_3$—C(OH)=) ppm. Benzene with increasing proportions of ether eluted cis-2-($\alpha$-dimethylamino-m-methoxymethoxybenzyl)1-methylcyclohexanol (II) as an oil NMR ($CDCl_3$): δ 2.26 (6H singlet, $N(CH_3)_2$), 1.15 (3H singlet $CH_3$—C(OH)=) ppm. Stereochemical assignments to the above compounds are based on the NMR of their $POCl_3$ -pyridine dehydration products showing that I affords a $\Delta^2$ olefin exclusively while II gave a $\Delta^1$ olefin as the major product together with a small amount of the $\Delta^2$-compound. The trans compound I on acid hydrolysis affords trans-2-($\alpha$-dimethylamino-m-hydroxybenzyl)-1-methylcyclohexanol m.p. 151°–153°, fumarate salt m.p. 177°–179°. The cis compound II (10.0 g.) in tetrahydrofuran (50 ml.) was treated with isopropanolic HCl (12.5 ml. 4.7 N) and allowed to stand overnight. After evaporation of solvent the residue was triturated with ammonia and ether. The ether extract was washed with water, brine, and dried ($Na_2SO_4$). Evaporation of the solvent afforded the highly crystalline cis-2-($\alpha$-dimethylamino-m-hydroxybenzyl)-1-methylcyclohexanol m.p. 175°–177°. Fumarate salt m.p. 199°–203° dec.

Found: C, 62.92; H, 7.69; N, 3.88. $C_{16}H_{25}NO_2 \cdot C_4H_4O_4$ requires: C, 63.30; H, 7.70; N, 3.69%. NMR (DMSO) δ 2.2 (6H singlet, $N(CH_3)_2$), 0.65 (3H singlet $CH_3$—C(OH)=) ppm.

EXAMPLE 41

Analgesic activity is demonstrated in rats by means of the following procedure, which is a modification of the procedure of D'Amour and Smith, J. Pharmocol. 72: 74, 1941.

Rats weighing approximately 150 to 200 g. are placed in individual holders, and each holder in turn is situated so that a high intensity light beam shines on the tip of the tail. The intensity of the light beam is adjusted so that normal rats respond by moving their tails out of the light beam in 3 to 8 seconds. The average of two readings taken 20 minutes apart serves as a pre-drug control. Rats are selected for use whose control readings agree within 1 second. Compounds are administered and reaction times are measured every 20 minutes for 2 hours. Analgesic agents cause a significant increase in reaction time.

| Compound | RESULTS Route | Dose mg/kg | No. Rats Showing Analgesia/No. Rats Tested |
| --- | --- | --- | --- |
| cis-2-(α-dimethylamino-m-methoxybenzyl)cyclo-hexanol hydrochloride | I.P. | 25.0 | 3/5 |
| cis-2-(α-dimethylamino-m-hydroxybenzyl)cyclo-hexanol hydrochloride | I.P. | 12.5 | 4/5 |
| | I.P. | 3.12 | 3/5 |
| | I.M. | 2.5 | 5/10 |
| | P.O. | 5.0 | 5/10 |
| cis-2-(α-dimethylamino-m-methoxybenzyl)cyclo-hexanol propionate hydrochloride | I.P. | 12.5 | 3/5 |
| | I.M. | 15.0 | 3/10 |
| cis-2-(α-dimethylamino-m-methoxymethoxybenzyl)cyclohexanol maleate | I.P. | 25.0 | 5/5 |
| | I.P. | 6.25 | 2/5 |
| | I.M. | 5.0 | 5/10 |
| | I.M. | 2.5 | 3/10 |
| cis-2-(α-dimethylamino-benzyl)cyclohexanol hydrochloride | I.P. | 12.5 | 8/10 |
| | I.P. | 6.25 | 9/10 |
| | I.M. | 6.25 | 8/10 |
| | P.O. | 5.0 | 6/10 |
| 1-cis-2-(α-dimethyl-amino-m-hydroxybenzyl)cyclohexanol hydro-chloride | I.P. | 6.25 | 6/10 |
| | I.P. | 3.12 | 8/10 |
| | I.M. | 0.62 | 7/10 |
| | I.M. | 0.41 | 4/10 |
| | P.O. | 6.25 | 7/10 |
| | P.O. | 3.12 | 5/10 |
| ED$_{50}$ for morphine in this procedure: | I.P. | 3.5 mg/kg | |
| | I.M. | 2.0 mg/kg | |
| | P.O. | 10.0 mg/kg | |

The subject matter which the applicants regard as their invention is particularly pointed out and distinctly claim as follows:

1. The process for producing analgesia in warm-blooded animals which comprises administering to a warm-blooded animal in need thereof an amount sufficient to produce analgesia in said warm-blooded animal of a compound of the formula:

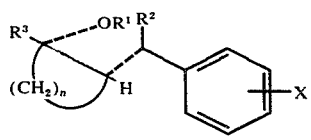

wherein $R^2$ is lower alkylamino, N-lower alkyl-N-methylamino, N-phenloweralkyl-N-methylamino, N-lower alkenyl-N-methylamino, N-cycloalkylmethyl-N-methylamino, or N-oxo-N-lower alkyl-N-methylamino; $R^3$ is hydrogen or methyl; and $R^1$ is hydrogen, lower alkyl, or lower alkylcarbonyl, and X is loweralkylcarbonyloxy; or $R^1$ is lower alkylcarbonyl and X is hydrogen, hydroxy, lower alkoxy, lower alkoxymethoxy, or halo; and $n$ is an integer of from 3 to 6; and a pharmacologically acceptable acid addition salt thereof.

2. The process of claim 1 wherein $n$ is 4.

3. The process of claim 1 wherein $n$ is 4 and $R^2$ is N-lower alkyl-N-methylamino.

4. The process of claim 1 wherein $n$ is 4, $R^2$ is dimethylamino, $R^3$ is hydrogen, $R^1$ is acetyl, and X is hydroxy.

5. The process of claim 1 wherein $n$ is 4, $R^2$ is dimethylamino, $R^3$ is hydrogen, $R^1$ is propionyl, and X is methoxy.

6. The process of claim 1 wherein $n$ is 4, $R^2$ is dimethylamino, $R^3$ is hydrogen, $R^1$ is acetyl, and X is hydrogen.

7. The process of claim 1 wherein $n$ is 4, $R^2$ is dimethylamino, $R^3$ is hydrogen, $R^1$ is hydroxy, and X is acetoxy.

8. The process of claim 1 wherein $n$ is 4, $R^2$ is dimethylamino, $R^3$ is hydrogen, $R^1$ is acetyl, and X is acetoxy.

9. The process of claim 1 wherein $n$ is 4, $R^2$ is dimethylamino, $R^3$ is methyl, $R^1$ is acetyl, and X is hydroxy.

* * * * *